United States Patent [19]
Parks et al.

[11] Patent Number: 4,739,014
[45] Date of Patent: Apr. 19, 1988

[54] METHOD OF CHEMICALLY BONDING ANTIOXIDANTS INTO POLYMERIC MATERIALS

[75] Inventors: Carl R. Parks, Akron; Dane K. Parker, Canton, both of Ohio

[73] Assignee: The Goodyear Tire & Rubber Company, Akron, Ohio

[21] Appl. No.: 474,841

[22] Filed: Mar. 14, 1983

Related U.S. Application Data

[63] Continuation of Ser. No. 277,302, Jun. 25, 1981, abandoned, which is a continuation of Ser. No. 106,208, Dec. 21, 1979, abandoned, which is a continuation of Ser. No. 494,130, Aug. 2, 1974, abandoned.

[51] Int. Cl.$^4$ .............................................. C08F 291/02
[52] U.S. Cl. ..................................... 525/263; 525/264; 525/265; 525/293; 525/296; 525/303
[58] Field of Search ............... 525/263, 264, 265, 293, 525/296, 303, 282

[56] References Cited

U.S. PATENT DOCUMENTS

| | | | |
|---|---|---|---|
| 3,658,769 | 4/1972 | Kline | 260/78 |
| 3,796,773 | 3/1974 | Coleman | 260/879 |
| 4,354,007 | 10/1982 | Scott | 525/370 |

OTHER PUBLICATIONS

Davis & Blake, "Chemistry and Technology of Rubber", Reinhold Pub. Co., New York, 1937, pp. 474–479.

Primary Examiner—Paul R. Michl
Attorney, Agent, or Firm—Alvin T. Rockhill

[57] ABSTRACT

A process for forming a polymer resistant to degradation comprising chemically bonding unsaturated antioxidants into polymeric materials by adding the antioxidant to the polymeric material, introducing a free radical initiator and causing the initiator to generate free radicals and bond the antioxidant to the polymeric material.

29 Claims, No Drawings

METHOD OF CHEMICALLY BONDING ANTIOXIDANTS INTO POLYMERIC MATERIALS

This is a continuation, of application Ser. No. 277,302, filed June 25, 1981, now abandoned, which is a continuation of Ser. No. 106,208, filed on Dec. 21, 1979, now abandoned, which is a continuation of Ser. No. 494,130 filed on Aug. 2, 1974, now abandoned.

This invention relates to a process for chemically bonding antioxidants into polymeric materials. More particularly this invention relates to antioxidants containing unsaturated segments and to a process of building the antioxidant into the polymeric material.

The advantages of building antioxidants into the chemical structure of polymers include the ability to resist extraction even after repeated exposure to aqueous detergent or dry-cleaning fluids. Such stabilized polymeric materials are used for carpet backing and applications where the polymer is used in solution form as in fabric treatments. These materials are also used in such applications as solvent hoses, oil seals and o-rings.

Chemically bound antioxidants have previously been incorporated in polymeric materials as a copolymerizable monomer during the polymerization stage of manufacture of the polymer. This polymerization requires the use of pure materials and specialized equipment and techniques. Network bound antioxidants have previously been prepared in natural rubber using nitrosodiphenylamine. In some cases antioxidants can also form resinous materials which are blended into the polymer. These high molecular weight materials are non-migrating and are not easily extracted.

It is an object of the present invention to provide a method for chemically bonding antioxidants containing aliphatic unsaturation in their structures into polymeric materials. Other objects will become apparent to those skilled in this art as the description proceeds.

It has now been discovered that antioxidants containing aliphatic unsaturation can be chemically bonded or built into the polymer network when mechanically blended with the polymer and then activated by a free radical generating material or initiator to cause the unsaturated antioxidant to react with the polymer by a free radical mechanism. Such materials can be added in free form to polymeric materials.

The preferred process comprises blending the antioxidant containing aliphatic unsaturation into the polymer, then blending a free radical initiator into the mixture at a temperature and for a time sufficient to cause the antioxidant to chemically bond with the polymer. Order of addition of the reactants can be varied.

The term "aliphatic unsaturation" as used herein is meant to describe unsaturation other than ring unsaturation. For example vinyl phenol has aliphatic unsaturation in the vinyl group and is effective in the present invention.

The invention has five parameters; polymer, free radical initiator, antioxidant, time and temperature. Each of the parameters can be varied to affect antioxidantpolymer chemical bonding.

Representative examples of polymers useful in the practice of the present invention are natural rubber, cispolyisoprene, cis-polybutadiene, styrene/butadiene, acrylonitrile/butadiene, polychloroprene, ethylene/propylene, and ethylene/propylene/diene polymer. Mixtures of these polymers can be used.

Representative examples of antioxidants containing aliphatic unsaturation useful in the practice of the present invention are N-(4-anilinophenyl)methacrylamide; 3-(3,5-di-t-butyl-4-hydroxyphenyl)butyl methacrylate; 3-(3,5-di-t-butyl-4-hydroxyphenyl)propyl methacrylate; the reaction product of allyl glycidyl ether and p-aminodiphenylamine containing 3-N-(4-anilinophenyl)amino-2-hydroxypropyl allyl ether; the reaction product of N-methylol maleimide and p-aminodiphenylamine containing N-[(4-anilinophenyl)amino methyl]-maleimide, and the reaction product of glycidyl methacrylate and p-aminodiphenylamine containing 3-N-(4'-anilinophenyl)amino-2-hydroxypropyl methacrylate. Mixtures of such antioxidants can be used.

Free radical initiators useful in the practice of the present invention are peroxides and high energy radiation. Representative examples of free radical initiators are peroxides such as lauroyl peroxide; benzoyl peroxide; dicumyl peroxide; di-t-butyl peroxide; 2,5-dimethyl-2,5-bis (2-ethylhexanoylperoxy)hexane; acetyl peroxide; t-butyl peroxymaleic acid; t-butyl peracetate; t-butyl hydroperoxide; t-butyl-peroxypivalate; t-butyl perbenzoate; t-butyl peroctoate; 2,4-dichlorobenzoyl peroxide; 1,1-bis(t-butylperoxy)-3,3,5-trimethylcyclohexane; $\alpha,\alpha'$-bis(t-butylhydroxy) diisopropylbenzene; 2,5-dimethyl-2,5-di(t-butylperoxy) hexane; 2,5-dimethyl-2,5-di(t-butylperoxy)hexyne-3; di(secbutyl)-peroxydicarbonate; t-butyl hydroperoxide; 2,5-dimethyl-2,5-di(hydroperoxy)hexane; cumene hydroperoxide; 1,1,3,3-tetramethylbutyl hydroperoxide; diisopropyl peroxydicarbonate; t-butyl peroxypivalate; t-butyl peroxyisobutyrate; t-butyl peracetate; 1,1,3,3-tetramethylbutyl peroxy-2-ethyl hexanoate; t-butylperoxy isopropyl carbonate; acetyl cyclohexylsulfonyl peroxide; isopropylbenzene dihydroperoxide; p-methane dihydroperoxide; t-butyl dihydroperoxide and t-butylperoxyisopropyl carbonate and radiation sources such as Cobalt 60. Mixtures of these free radical initiators can be used.

Concentrations of antioxidants useful in the present invention are from about 0.2 part to about 10 parts per 100 parts by weight of polymeric material, but from about 1 part to about 3 parts per 100 parts by weight of polymeric material are preferred.

Concentrations of free radical initiators useful in the present invention are from about 0.1 part to about 5 parts per 100 parts by weight of polymeric material, but from about 0.5 part to about 2 parts per 100 parts by weight of polymeric material are preferred. When using free radical initiation from high energy sources such as Cobalt 60, a level of radiation of about 5 to about 100 megarads can be used, but from 20 to 50 megarads is preferred.

The blending of the antioxidant and the free radical initiator into the polymer is carried out at a temperature of from about 20° C. to 160° C., with a range of from about 50° C. to 100° C. being preferred for as long a period of time as is necessary to accomplish the chemical bonding. Time for the bonding reaction to be completed usually ranges from about one-half minute to about sixty minutes, but from about two to about ten minutes is usually sufficient.

In aqueous rubber latex, the reaction time and temperature are generally different than employed with the dry rubber. The invention is also useful for polymers made in organic solution such as hexane and pentane. Examples of such polymers include cis-polyisoprene, cis-polybutadiene, ethylene propylene rubber (EPR)

and ethylene/propylene/diene rubber (EPDM). Blending in latex is usually carried out for from about 2 hours to 24 hours at a temperature of from about 20° C. to 90° C.

Selection of free radicals initiators is made based on the method of reaction and the temperatures used. Methods of blending polymers and of adding materials are well known to those skilled in this art. For example, blending on a mill requires that a free radical initiator be used which has a longer half-life than if blending is accomplished using a Banbury internal mixer. Temperature developed during the mixing cycle also determines the type of free radical initiator needed.

Practice of the invention is illustrated in the examples below. All parts and percentages are by weight unless otherwise specified. The procedure used for preparing and testing the polymer samples is illustrated below using natural rubber as a typical polymer.

Natural rubber was milled for five minutes at 55° C. to 60° C. The rubber was sheeted from the mill at approximately 0.020 inch gauge. Strips were cut from the sheet and extracted with acetone for ten days at room temperature, changing the solvent every other day. Oxygen absorption measurements were made at 90° C. The testing procedure is fully detailed in Industrial and Engineering Chemistry, 43, page 456 (1951) and Industrial and Engineering Chemistry, 45, page 392 (1953).

The antioxidants used are named and described as follows:

(A) N-(4-anilinophenyl)methacrylate whose method of preparation is well known in the art and described in U.S. Pat. No. 3,658,769.

(B) 4-(3,5-Di-t-butyl-4-hydroxyphenyl)-2-butyl methacrylate was prepared in the following manner.

A two-liter flask was charged with 105 grams (1.05 moles) acetyl acetone, 142 grams (1.025 moles) $K_2CO_3$ and one liter of ethanol. Over a one hour period 254 grams (1.0 mole) of 3,5-di-t-butyl-4-hydroxy benzyl chloride was added dropwise. A monoalkylated diketone formed, thickening the mixture. The mixture was heated to a vigorous reflux for six hours and then cooled to room temperature. Sodium borohydride, 15 grams (0.4 mole) was added slowly over a 15 minute period. The mixture was stirred at 40° C. for four hours and allowed to stand overnight at room temperature. The mixture was then hydrolyzed with dilute 1:1 concentrated hydrochloric acid and water. Hydrolysis was considered to be complete when gas evolution ceased. Potassium chloride salt was removed from the mixture by filtration and ethanol removed by distillation. The residue was poured into excess cooled water and allowed to stand until crystallization was complete, about 1 to 2 hours. The product was removed from solution and allowed to air dry.

The product, 69.5 grams (0.25 mole) was placed in a one liter flask with 350 milliliters of methyl methacrylate, 0.5 gram hydroquinone and 5 grams tetraisopropyl titanate. The mixture was heated to reflux and a methanol-methylmethacrylate azeotrope was removed over a 3½ hour period. The reaction flask was cooled slightly 20 milliliters water was added dropwise to hydrolyze the catalyst. The reaction mixture was cooled to room temperature and 3 grams sodium carbonate was added. The reaction mixture was stirred for 15 minutes after the addition of sodium carbonate and then filtered. One hundred milliliters of hexane was added to the filtrate forming two phases. The organic phase was removed, dried over magnesium sulfate and the solvent was evaporated to obtain 82 grams (95%) of 4-(3,5-di-t-butyl-4-hydroxy phenyl-2-butyl methacrylate.

(C) 3-(3,5-Di-t-butyl-4-hydroxyphenyl)propyl methacrylate was prepared in the following manner.

The preparation was the same as that described for antioxidant (B) except that 66 grams (0.25 mole) of 3(3,5-di-t-butyl-4-hydroxyphenyl)propanol was used in place of 69.5 grams (0.25 mole) of 4-(3,5-di-t-butyl-4-hydroxy phenyl)-2-butanol.

(D) The reaction product of N-methylolmaleimide and p-aminodiphenylamine was prepared in the following fashion. Maleimide (49 grams) was placed in suspension with 40.5 milliliters of 37 percent formalin. A 5 percent aqueous solution of sodium hydroxide (1.5 milliliters) was added to the mixture at 30° C. The mixture cleared in an hour and the product crystallized after standing overnight. The N-methylolmaleimide was filtered and washed with cold ether to yield 49.6 grams of product having a melting point between 95° C. and 98° C.

N-methylolmaleimide (40 grams) was added to 100 milliliters of dioxane in a 500 milliliter flask with stirring and under a nitrogen purge. Distilled p-aminodiphenylamine (58.9 grams) was added and the mixture heated to reflux. The dioxane was removed on a rotary evaporator and the product used without further purification. The product was predominantly N-[(4-anilinophenyl)aminomethyl] maleimide.

(E) The reaction product of allyl glycidyl ether and p-aminodiphenylamine was prepared in the following manner: p-Aminodiphenylamine (184 grams) and 138 grams of allyl glycidyl ether were placed in a two-liter flask. Isopropanol (800 milliliters) was added and the mixture was refluxed for 8 hours under a slow nitrogen purge. The isopropanol was removed on a rotary evaporator and 316 grams of product was used without further purification. The antioxidant product was predominantly 3-N-(4'-anilinophenyl) amino-2-hydroxypropyl allyl ether.

(F) 3,5-Di-t-butyl-4-vinylphenol was prepared in the following manner.

Five grams of 4-ethylidene-2,6-di-t-butylcyclohexa-2,5-dienone, 5 to 10 grams of anhydrous neutral $Al_2O_3$ and 75 milliliters of petroleum ether were charged into a round bottomed flask. The flask was stirred with a magnetic stirrer while heated to a temperature between 70° C. and 80° C. for 30 to 60 minutes. The mixture was cooled and the petroleum ether removed to yield a residue which was recrystallized from acetone at −78° C. to give 3,5-di-t-butyl-4-vinylphenol in 95 to 100 percent yield.

(G) The reaction product of glycidyl methacrylate and p-aminodiphenylamine was obtained using the following procedure. p-Aminodiphenylamine (184 grams) and 138 grams of glycidyl methacrylate were placed in a two-liter flask. Isopropanol (800 milliliters) was added and the mixture was refluxed for 8 hours under a slow nitrogen purge. The isopropanol was removed on a rotary evaporator, 316 grams of product being obtained. The product was used without further purification. The antioxidant was predominantly 3-N-(4'-anilinophenyl)amino-2-hydroxypropyl methacrylate.

Example 2 shows two parts per 100 parts of the extracted rubber of antioxidant (A) using the same procedure as described in Example 1. In Examples 3 to 5, two parts per hundred rubber of a free radical initiator, lauroyl peroxide, was added both separately and with triethanolamine and compared to triethanolamine added along. The test strips were tested for oxygen absorption both before and after extraction in acetone.

Duplicate test strips were heated for an additional 30 minutes at 120° C. in a curing press and again checked with and without being extracted in acetone. The results are shown in Table I.

TABLE I

| Example | 1 | 2 | 3 | 4 | 5 |
|---|---|---|---|---|---|
| Natural rubber | 100 | → | → | → | → |
| Antioxidant A | 0 | 2 | → | → | → |
| Triethanolamine | | | 2 | | 2 |
| Lauroyl peroxide | | | | 2 | 2 |
| Hours to 1% Oxygen at 90° C. | | | | | |
| As is | 229 | 422 | 465 | 695 | 458 |
| Acetone extracted | 9 | 81 | 55 | 243 | 225 |
| Hours to 1% Oxygen at 90° C. after heating | | | | | |
| As is | 216 | 334 | 481 | 555 | 484 |
| Acetone extracted | 9 | 80 | 107 | 245 | 329 |

EXAMPLES 6-8

Similar experiments using the same procedure as described in Examples 1 to 5 were carried out in styrene/butadiene rubber using antioxidant (B) as the additive. After test strips were cut from the milled sheet, they were heated in a press for 30 minutes at 120° C. and then extracted for 48 hours in a Soxhlet apparatus with acetone. Oxygen absorption measurements were then made as described in Example 1 except that a temperature of 100° C. was used. The results are given in Table II.

TABLE II

| Example | 6 | 7 | 8 |
|---|---|---|---|
| SBR-1502 | 100 | → | → |
| Antioxidant B | 2 | → | → |
| t-Butyl peroctoate | 3 | | |
| Benzoyl peroxide | | 3 | |
| Lauroyl peroxide | | | 3 |
| Hours to 1% Oxygen at 100° C. | | | |
| Acetone extracted | 235 | 185 | 280 |

EXAMPLES 9-11

Further experiments were made in natural rubber using antioxidants of allyl and maleimide derivatives as the additives. Dicumyl peroxide was used as the free radical initiator. The samples were cured for 45 minutes at 150° C. and then extracted with acetone in a Soxhlet apparatus for 48 hours. Oxygen absorption measurements were then made at 90° C. as described in Example 1. The results are shown in Table III.

TABLE III

| Example | 9 | 10 | 11 |
|---|---|---|---|
| Natural rubber | 100 | → | → |
| Dicumyl peroxide | 1.25 | → | → |
| Antioxidant C | 2 | | |
| Antioxidant D | | 2 | |
| Antioxidant E | | | 2 |
| Hours to 1% Oxygen at 90° C. | | | |
| Acetone extracted | 528 | 380 | 365 |

EXAMPLES 12-16

Additional experiments were made in natural rubber using dicumyl peroxide as the free radical initiator which tested various additives including vinyl compounds such as antioxidant (F). The procedure in all tests was the same as was used to produce the results in Table III. The results are shown in Table IV.

TABLE IV

| Example | 12 | 13 | 14 | 15 | 16 |
|---|---|---|---|---|---|
| Natural rubber | 100 | → | → | → | → |
| Dicumyl peroxide | 0.5 | → | → | → | → |
| Antioxidant F | | 2 | | | |
| Antioxidant C | | | 2 | | |
| Antioxidant G | | | | 2 | |
| Antioxidant A | | | | | 2 |
| Hours to 1% Oxygen at 90° C. | | | | | |
| Acetone extracted | 10 | 275 | 505 | 550 | 250 |

The examples given in the above tables show several antioxidants built into the polymer using the process of this invention. These antioxidants give protection to the extracted vulcanizates particularly when a peroxide such as dicumyl peroxide is used as a curative.

In Examples 17 through 20, dicumyl peroxide was used as the free radical initiator in ethylene/propylene/diene (EPDM) and ethylene/propylene (EPR) rubbers. The samples were cured for 45 minutes at 150° C. and then extracted with acetone in a Soxhlet apparatus for 48 hours. Oxygen absorption measurements were then made as described in Example 1 except that 120° C. was used.

TABLE V

| Example | 17 | 18 | 19 | 20 |
|---|---|---|---|---|
| EPR | 100 | → | | |
| EPDM | | | 100 | → |
| HAF Black | 50 | → | → | → |
| Processing oil | 10 | → | → | → |
| Dicumyl peroxide | 2.5 | → | → | → |
| Antioxidant A | | 1.5 | | 1.5 |
| Hours to 1% Oxygen at 120° C. | | | | |
| Acetone extracted | 164 | 186 | 189 | 260 |

Examples 21-25 show the effect of varying the rubber while using the same antioxidant. The results are shown in Table VII.

TABLE VII

| Example | 21 | 22 | 23 | 24 | 25 |
|---|---|---|---|---|---|
| Antioxidant G | 2 | → | → | → | → |
| Natural rubber | 100 | | | | |
| Polyisoprene | | 100 | | | |
| Styrene/Butadiene | | | 100 | | |
| Acrylonitrile/Butadiene | | | | 100 | |
| Chloroprene | | | | | 100 |
| Lauroyl peroxide | 1 | → | → | → | → |
| Hours to 1% Oxygen at 100° C., Unextracted | | | | | |
| | 180 | 291 | 113 | 145 | 27 |
| Hours to 1% Oxygen at 100° C., Acetone Extracted | | | | | |
| | 93 | 122 | 95 | 147 | 52 |

While certain representative embodiments and details have been shown for the purpose of illustrating the invention, it will be apparent to those skilled in this art that various changes and modifications may be made therein without departing from the spirit or scope of the invention.

We claim:
1. A process for preparing an oxidatively stable polymer which comprises reacting the polymer with an antioxidant containing aliphatic unsaturation, said antioxidant rendering the polymer less susceptible to oxidative attack by chemically interrupting the autoxidation process by which the polymer is oxidatively degraded, the reaction between the polymer and the antioxidant being carried out in the presence of a free radical said free radical being generated by a free radical generator selected from the group consisting of lauroyl peroxide; benzoyl peroxide; dicumyl peroxide; di-t-butyl peroxide; 2,5-dimethyl-2,5-bis(2-ethylhexanoylperoxy)hexane; acetyl peroxide; t-butyl peroxymaleic acid; t-butyl peracetate; t-butyl hydroperoxide; t-butyl-peroxypivalate; t-butyl perbenzoate; t-butyl peroctoate; 2,4-dichlorobenzoyl peroxide; 1,1-bis(t-butylperoxy)-3,3,5-trimethylcyclohexane; α,α'-bis(t-butylhydroxy)diisopropylbenzene; 2,5-dimethyl-2,5-di(t-butylperoxy)hexane; 2,5-dimethyl-2,5-di(t-butylperoxy)hexane-3; di(sec-butyl)peroxydicarbonate; t-butyl hydroperoxide; 2,5-dimethyl-2,5-di(hydroperoxy)hexane; cumene hydroperoxide; 1,1,3,3-tetramethylbutyl hydroperoxide; diisopropyl peroxydicarbonate; t-butyl peroxypivalate; t-butyl peroxyisobutyrate; t-butyl peracetate; 1,1,3,3-tetramethylbutylperoxy-2-ethyl hexanoate; t-butylperoxy isopropyl carbonate; acetyl cyclohexylsulfonyl peroxide; isopropylbenzene dihydroperoxide; p-methane dihydroperoxide; t-butyl dihydroperoxide and t-butylperoxyisopropyl carbonate said generator producing said free radicals at a temperature of 20° C. to 160° C.

2. A process according to claim 1 in which the antioxidant is a vinyl group-containing antioxidant.

3. A process according to claim 1 in which the antioxidant is a compound of the formula:

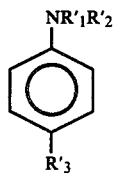

in which $R'_1$, and $R'_3$ represent hydrogen atoms and in which $R'_2$ is an aryl radical having a structural formula selected from the group consisting of

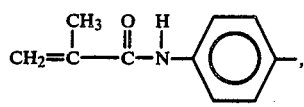

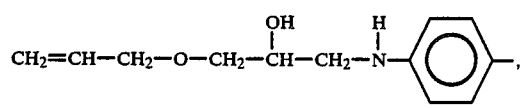

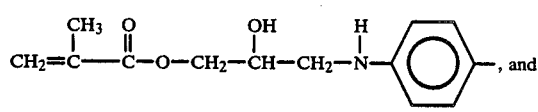

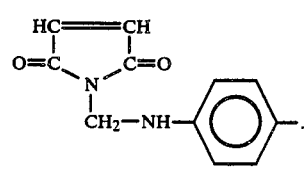

4. A process according to claim 2 in which the antioxidant has the formula:

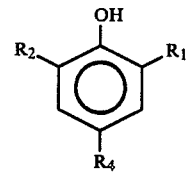

wherein $R_1$ and $R_2$ are t-butyl radicals and wherein $R_4$ represents a

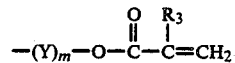

in which $R_3$ is a methyl radical, in which Y is a propylene or butylene radical, and in which m is 1.

5. A process according to claim 4 in which the antioxidant is selected from the group consisting of 3-(3,5-di-t-butyl-4-hydroxyphenyl)propyl methacrylate and 3-(3,5-di-t-butyl-4-hydroxyphenyl) butyl methacrylate.

6. A process according to claim 1 in which the antioxidant is a di(aryl)amine in which one of the aryl groups is substituted by a vinyl-terminated group.

7. A process according to claim 1 in which the polymer is reacted as an aqueous emulsion or latex.

8. A process according to claim 1 in which the polymer is unsaturated.

9. A process according to claim 1 in which the polymer is a natural or synthetic rubber latex.

10. A process according to claim 1 in which the polymer is a solid natural or synthetic rubber.

11. A process according to claim 1 in which the polymer is a synthetic rubber.

12. A process according to claim 2 in which the antioxidant has the formula:

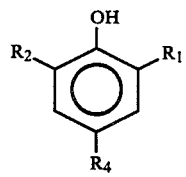

wherein $R_1$ and $R_2$ are t-butyl radicals and wherein $R_4$ represents a

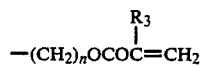

radical in which $R_3$ is a methyl radical and wherein n is 3.

13. A process according to claim 1 wherein said generator produces free radicals at a temperature of 50° C. to 100° C.

14. A process according to claim 1 wherein said antioxidant is a chain-breaking antioxidant.

15. A process for chemically bonding an antioxidant containing an aliphatic unsaturation to a solid diene polymer which comprises mixing the antioxidant selected from the group consisting of N-(4-anilinophenyl)methacrylamide, 3-(3,5-di-t-butyl-4-hydroxyphenyl)butyl methacrylate, 3-(3,5-di-t-butyl-4-hydroxyphenyl)propyl methacrylate, the reaction product of allyl glycidyl ether and p-aminodiphenylamine containing 3-N-(4-anilinophenyl)amino-2-hydroxypropyl allyl ether, the reaction product of hydroxymethylmaleimide and p-aminodiphenylamine containing N-[4-anilinophenyl)aminomethyl]maleimide, and the reaction product of glycidyl methacrylate and p-aminodiphenylamine containing 3-N-(4-anilinophenyl)amino-2-hydroxypropyl methacrylate, the solid diene polymer, and a peroxide selected from the group consisting of lauroyl peroxide, benzoyl peroxide, dicumyl peroxide, di-t-butyl peroxide, 2,5-dimethyl-2,5-bis(2-ethylhexanoylperoxy)hexane, acetyl peroxide, t-butyl peroxymaleic acid, t-butyl peracetate, t-butyl hydroperoxide, t-butyl peroxypivalate, t-butyl perbenzoate, t-butyl peroctoate, 2,4-dichlorobenzoyl peroxide, 1,1-bis(t-butylperoxy)-3,3,5-trimethylcyclohexane, α,α'-bis(t-butylhydroxy)-diisopropylbenzene, 2,5-dimethyl-2,5-di(t-butylperoxy)-hexane, di(sec-butyl)peroxydicarbonate, diisopropyl peroxydicarbonate, t-butyl peroxypivalate, t-butyl peroxyisobutyrate, t-butyl peracetate, 1,1,3,3-tetramethylbutyl peroxy-2-ethyl hexanoate, t-butylperoxy isopropyl carbonate, acetylcyclohexylsulfonyl peroxide, t-butylperoxyisopropyl carbonate, t-butyl hydroperoxide, 2,5-dimethyl-2.5-di(hydroperoxy)hexane, cumene hydroperoxide, 1,1,3,3-tetramethylbutyl hydroperoxide, isopropylbenzene dihydroperoxide, p-methane dihydroperoxide and t-butyl dihydroperoxide, and heating and reacting the mixture in the solid form to cause the polymer and the antioxidant to chemically bond together.

16. A process for chemically bonding an antioxidant containing an aliphatic unsaturation to a solid diene polymer which comprises mixing the antioxidant selected from the group consisting of N-(4-anilinophenyl)methacrylamide, 3-(3,5-di-t-butyl-4-hydroxyphenyl)butyl methacrylate, 3-(3,5-di-t-butyl-4-hydroxyphenyl)propyl methacrylate, the reaction product of allyl glycidyl ether and p-aminodiphenylamine containing 3-N-(4-anilinophenyl)amino-2-hydroxypropyl allyl ether, the reaction product of hydroxymethylmaleimide and p-aminodiphenylamine containing N-[4-anilinophenyl)aminomethyl]maleimide, and the reaction product of glycidyl methacrylate and p-aminodiphenylamine containing 3-N-(4-anilinophenyl)amino-2-hydroxypropyl methacrylate, a solid diene polymer selected from the group consisting of natural rubber, cis-polyisoprene rubber, polybutadiene rubber, styrene/butadiene rubber acrylonitrile/butadiene rubber, ethylene/propylene rubber and ethylene/propylene/diene rubber and a peroxide selected from the group consisting of lauroyl peroxide, benzoyl peroxide, dicumyl peroxide, di-t-butyl peroxide, 2,5-dimethyl-2,5-bis(2-ethylhexanoylperoxy)hexane, acetyl peroxide, t-butyl peroxymaleic acid, t-butyl peracetate, t-butyl hydroperoxide, t-butyl peroxypivalate, t-butyl perbenzoate, t-butyl peroctoate, 2,4-dichlorobenzoyl peroxide, 1,1-bis(t-butylperoxy)-3,3,5-trimethylcyclohexane, α,α'-bis(t-butylhydroxy)-diisopropylbenzene, 2,5-dimethyl-2,5-di(t-butylperoxy)-hexane, di(sec-butyl)peroxydicarbonate, diisopropyl peroxydicarbonate, t-butyl peroxypivalate, t-butylperoxyisobutyrate, t-butylperacetate, 1,1,3,3-tetramethylbutyl peroxy-2-ethyl hexanoate, t-butylperoxy isopropyl carbonate, acetylcyclohexylsulfonyl peroxide, t-butylperoxyisopropyl carbonate, t-butyl hydroperoxide, 2,5-dimethyl-2,5-di(hydroperoxy) hexane, cumene hydroperoxide, 1,1,3,3-tetramethylbutyl hydroperoxide, isopropylbenzene dihydroperoxide, p-methane dihydroperoxide and t-butyl dihydroperoxide, and wherein the chemical bonding is carried out at a temperature of from 20° C. to 160° C.; wherein the chemical bonding is carried out for from about 0.5 minutes to about 60 minutes; and wherein the peroxide is present in the amount of from about 0.10 to about 5 parts by weight per 100 parts by weight of the diene polymer.

17. A process for preparing an oxidatively stable polymer which comprises reacting the polymer with an antioxidant containing aliphatic unsaturation, said antioxidant rendering the polymer less susceptible to oxidative attack by chemically interrupting the autoxidation process by which the polymer is oxidatively degraded, the reaction between the polymer and the antioxidant being carried out in the presence of a free radical which is produced by high energy radiation, said reaction being carried out at a temperature of 20° C. to 160° C.

18. A process according to claim 17 in which the antioxidant is a vinyl group-containing antioxidant.

19. A process according to claim 17 in which the antioxidant is a compound of the formula:

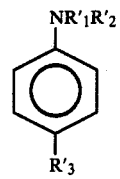

in which R'$_1$, and R'$_3$ represent hydrogen atoms and in which R'$_2$ is an aryl radical having a structural formula selected from the group consisting of

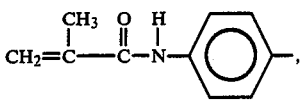

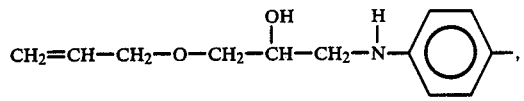

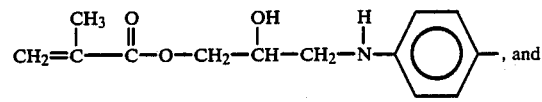

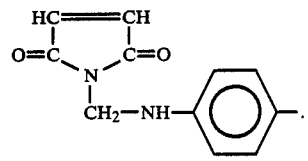

20. A process according to claim 17 in which the antioxidant has the formula:

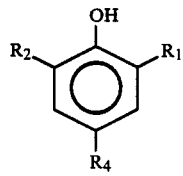

wherein R$_1$ and R$_2$ are t-butyl radicals and wherein R$_4$ represents a

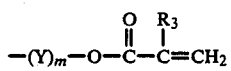

radical in which $R_3$ is a methyl radical, in which Y is a propyl or butyl radical, and in which m is 1.

21. A process according to claim 17 in which the antioxidant is selected from the group consisting of 3-(3,5-di-t-butyl-4-hydroxyphenyl)propyl methacrylate and 3-(3,5-di-t-butyl-4-hydroxyphenyl)butyl methacrylate.

22. A process according to claim 17 in which the antioxidant is a di(aryl)amine in which one of the aryl groups is substituted by a vinyl-terminated group.

23. A process according to claim 17 in which the polymer is reacted as an aqueous emulsion or latex.

24. A process according to claim 17 in which the polymer is unsaturated.

25. A process according to claim 17 in which the polymer is a natural or synthetic rubber latex.

26. A process according to claim 17 in which the polymer is a solid natural or synthetic rubber.

27. A process according to claim 17 in which the polymer is a synthetic rubber.

28. A process according to claim 17 wherein said reaction is carried out at a temperature of 50° C. to 100° C.

29. A process according to claim 17 wherein said antioxidant is a chain-breaking antioxidant.

* * * * *